United States Patent [19]

Samaan

[11] Patent Number: 4,658,039

[45] Date of Patent: Apr. 14, 1987

[54] PROCESS FOR THE PREPARATION OF ALKENYL ESTERS OF ACEMETACIN

[75] Inventor: Samir Samaan, Wuppertal, Fed. Rep. of Germany

[73] Assignee: Bayer Aktiengesellschaft, Leverkusen, Fed. Rep. of Germany

[21] Appl. No.: 800,493

[22] Filed: Nov. 21, 1985

[30] Foreign Application Priority Data

Dec. 1, 1984 [DE] Fed. Rep. of Germany ....... 3443993

[51] Int. Cl.$^4$ ........................................... C07D 209/28
[52] U.S. Cl. ..................................... 548/501; 548/500
[58] Field of Search ......................................... 548/501

[56] References Cited

U.S. PATENT DOCUMENTS 4,503,237  3/1985  Gnehm et al. ...................... 548/500

Primary Examiner—Glennon H. Hollrah
Assistant Examiner—D. B. Springer
Attorney, Agent, or Firm—Sprung Horn Kramer & Woods

[57] ABSTRACT

The new indole derivatives of the formula

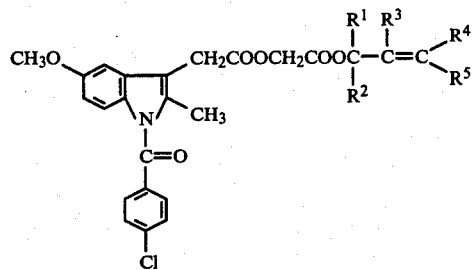

in which
  $R^1$ and $R^2$ are identical or different and denote hydrogen or lower alkyl,
  $R^3$ denotes hydrogen, lower alkyl or halogen and
  $R^4$ and $R^5$ are identical or different and denote hydrogen, lower alkyl or optionally substituted aryl, and
  $R^4$ and $R^5$ can also represent lower alkenyl, and
wherein
  $R^2$ and $R^5$ can be linked by an alkylene bridge of the formula $$-CH_2-CH_2-CH_2)_n$$

in which
  n represents the number 0 or 1, can be prepared by reacting an ammonium or phosphonium salt of the corresponding indolecarboxylic acid with a haloacetic acid allyl ester. The new compounds can be used to prepare acemetacin. The new indole derivatives possess a pharmacological action.

2 Claims, No Drawings

PROCESS FOR THE PREPARATION OF ALKENYL ESTERS OF ACEMETACIN

The invention relates to new indole derivatives, to a process for their preparation, to their use for the preparation of acemetacin and to their use as medicaments.

The preparation of the indole derivatives 1-(p-chlorobenzoyl)-5-methoxy-2-methylindole-3-acetoxyacetate tetrahydropyranyl ester and of the corresponding furanyl ester (the so-called acemetacin tetrahydropyranyl ester and furanyl ester) are known from European Pat. No. 0,087,655. Similar compounds are described in European Pat. Nos. 0,088,252 and 0,087,657.

There have been found new indole derivatives of the formula

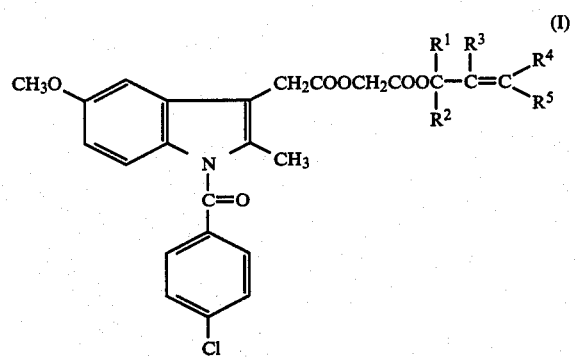

in which
R$^1$ and R$^2$ are identical or different and denote hydrogen or lower alkyl,
R$^3$ denotes hydrogen, lower alkyl or halogen and
R$^4$ and R$^5$ are identical or different and denote hydrogen, lower alkyl or optionally substituted aryl, and
R$^4$ and R$^5$ can also represent lower alkenyl, and
wherein
R$^2$ and R$^5$ can be linked by an alkylene bridge of the formula —CH$_2$—CH$_2$—CH$_2$)$_n$ in which
n represents the number 0 or 1.

The new indole derivatives are 1-(p-chlorobenzyl)-5-methoxy-2-methylindole-3-acetoxyacetic acid allyl esters (acemetacin allyl esters).

They can be used particularly advantageously for the preparation of acemetacin. Acemetacin allyl esters themselves have an important pharmacological action.

Within the scope of the present invention, lower alkyl in general denotes a straight-chain or branched hydrocarbon radical with 1 to about 6 carbon atoms. The following lower alkyl radicals may be mentioned as examples: methyl, ethyl, propyl, isopropyl, butyl, isobutyl, pentyl, isopentyl, hexyl and isohexyl. Particularly preferred lower alkyl radicals are methyl and ethyl.

Within the scope of the present invention, lower alkenyl in general denotes an unsaturated, straight-chain or branched hydrocarbon radical with 2 to about 6 carbon atoms and preferably with one double bond. The following lower alkenyl radicals may be mentioned as examples: vinyl, allyl, but-2-enyl and pent-2-enyl.

Within the scope of the present invention, halogen in general denotes fluorine, chlorine, bromine or iodine, preferably chlorine.

Within the scope of the present invention, aryl in general denotes an aromatic hydrocarbon radical with 6 to 12 carbon atoms. The following aryl radicals may be mentioned as examples: phenyl, biphenyl, naphthyl and benzyl. The preferred aryl radical is phenyl.

The aryl radicals can optionally be substituted. In that case, the aryl radical is in general substituted by 1 to 3, preferably 1 or 2, radicals.

As possible radicals there may be mentioned halogens, such as fluorine, chlorine, bromine or iodine, preferably chlorine, or lower alkyl (C$_1$ to about C$_6$), preferably methyl and ethyl.

If the radicals R$^2$ and R$^5$ are linked by an alkylene bridge, cyclopentenyl or cyclohexenyl rings result.

Indole derivatives of the formula

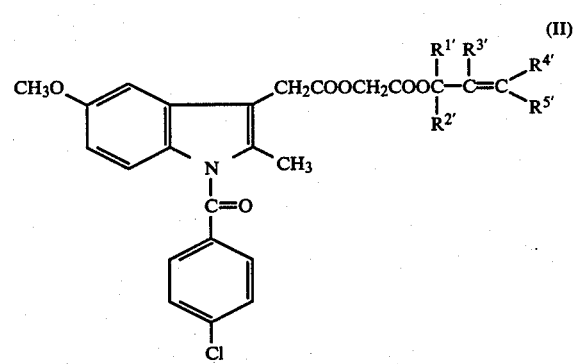

in which
R$^{1'}$ and R$^{2'}$ are identical or different and denote hydrogen, methyl or ethyl,
R$^{3'}$ denotes hydrogen, methyl, ethyl or chlorine and
R$^{4'}$ and R$^{5'}$ are identical or different and denote hydrogen, methyl, ethyl, phenyl, benzyl, tolyl or 4-chlorophenyl,
and wherein
R$^{2'}$ and R$^{5'}$ can be linked by the radical

—CH$_2$—CH$_2$—CH$_2$— are preferred.

Specifically, the following acemetacin allyl esters may be mentioned: acemetacin allyl ester, acemetacin methallyl ester, acemetacin cinnamyl ester, acemetacin-2-chloroallyl ester, acemetacin crotyl ester, acemetacin p-chlorocinnamyl ester, acemetacin cyclohexenyl ester and acemetacin hexadienyl ester.

Acemetacin allyl ester is particularly preferred.

There has also been found a process for the preparation of the new indole derivatives, which is characterized in that salts of indolecarboxylic acid, of the formula

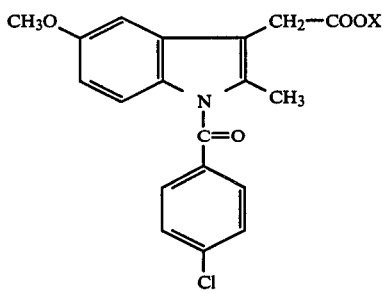

in which x represents hydrogen or an ammonium or phosphonium radical, are reacted with a haloacetic acid allyl ester of the formula

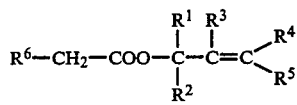

in which

R$^1$ and R$^2$ are identical or different and denote hydrogen or lower alkyl,

R$^3$ denotes hydrogen, lower alkyl or halogen and

R$^4$ and R$^5$ are identical or different and denote hydrogen, lower alkyl or optionally substituted aryl, and R$^4$ and R$^5$ can also represent lower alkenyl and wherein R$^2$ and R$^5$ can be linked by an alkylene bridge of the formula CH$_2$—CH$_2$—CH$_2$)$_n$ in which n represents the number 0 or 1, and R$^6$ represents halogen in the presence of solvents, in the temperature range from −30° to +110° C.

The process according to the invention can be illustrated by the following equation:

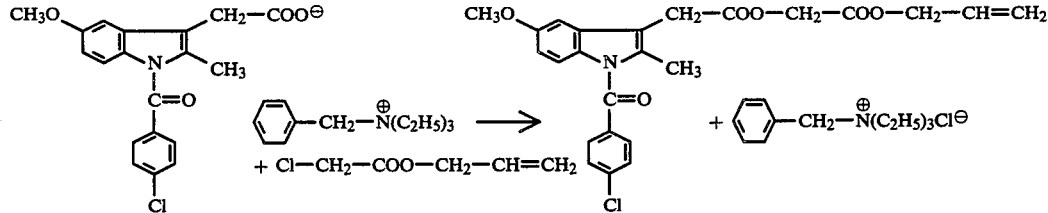

The ammonium and phosphonium salts of the indolecarboxylic acid used for the process according to the invention are known per se (Arzneimittelforschung 30, 1314 (1980).

As ammonium or phosphonium radicals there may be mentioned radicals of the formula

in which

M represents nitrogen or phosphorus and

Y$^1$ to Y$^4$ are identical or different and denote hydrogen, alkyl, cycloalkyl or aryl.

Alkyl here denotes, according to the invention, a straight-chain or branched hydrocarbon radical with 1 to about 12 carbon atoms. The following alkyl radicals may be mentioned as examples: methyl, ethyl, propyl, isopropyl, butyl, isobutyl, pentyl, isopentyl, hexyl and isohexyl.

Aryl here denotes, according to the invention, an aromatic hydrocarbon radical with 6 to 12 carbon atoms. Phenyl, biphenyl, benzyl and naphthyl may be mentioned as examples.

Cycloalkyl here denotes, according to the invention, a cyclic hydrocarbon radical with 4 to 8, preferably 5 or 6, carbon atoms. The following cycloalkyl radicals may be mentioned as examples: cyclobutyl, cyclopentyl, cyclohexyl, cycloheptyl and cyclooctyl.

Tertiary or quanternary ammonium salts with methyl, ethyl, phenyl and benzyl radicals are particularly preferred.

Haloacetic acid allyl esters for the process according to the invention are known per se (J. Polymer. Sci. 3, 278 (1948), C.A. 2632 (1949)) and can be prepared, for example, by reaction of haloacetic acids and allyl alcohols or from chloroacetyl chloride or bromoacetyl bromide and allyl alcohols in the presence of a base, for example aniline. The following haloacetic acid allyl esters may be mentioned as examples: allyl chloroacetate, 1-cinnamyl chloroacetate, α-methallyl chloroacetate, allyl bromoacetate, α-methallyl bromoacetate, cyclohexenyl chloroacetate, α-chloroallyl chloroacetate, p-chlorocinnamyl chloroacetate, hexadienyl chloroacetate and crotyl chloroacetate.

Preferred haloacetic acid allyl esters for the process according to the invention are allyl chloroacetate, α-methallyl chloroacetate and cinnamyl chloroacetate.

The process according to the invention is in general carried out at a temperature ranging from −30° to +110° C., preferably from 0° to 50° C.

The process according to the invention is in general carried out under normal pressure. It is however also possible to carry out the process under reduced pressure or superatmospheric pressure, for example in the pressure range from 1 to 6 bar. Solvents for the process according to the invention are, in general, inert organic solvents. Polar aprotic solvents, such as, for example, chloroform, methylene chloride, dimethylformamide, hexamethylphosphorotriamide and formamide are preferred.

In a particular embodiment of the process according to the invention, the reaction is carried out in a two-phase reaction. For this it is possible to work in a liquid-liquid two-phase system, with water constituting the second phase, or in a solid-liquid two-phase system with the indolecarboxylic acid or its salts as the crystalline phase. Organic solvents particularly preferred for such reactions are toluene, methylene chloride, ethyl acetate, chloroform, acetone and methyl isobutyl ketone.

In carrying out the process according to the invention in a two-phase system, a phase transfer catalyst is generally added.

Phase transfer catalysts for the process according to the invention can be compounds of the formula

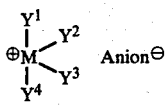 (IV)

in which
$Y^1$ to $Y^4$ have the abovementioned meaning and the anion is an inorganic or organic acid radical.

Anions can be, for example, halides, preferably chlorides and bromides, sulphates and bisulphates or acetates.

The following phase transfer catalysts may be mentioned as preferred: benzyltriethylammonium chloride, tetrabutylammonium bromide, tetrabutylammonium bisulphate, methyltrioctylammonium chloride, tetrabutylphosphonium bromide and hexadecyltributylphosphonium bromide.

The phase transfer catalyst is in general employed in an amount of 0.05 to 20 mole %, preferably of 1 to 10 mole %, based on the indolecarboxylic acid.

When using the free indolecarboxylic acid, the process according to the invention is preferably carried out in the presence of bases. As bases there may be mentioned alkali metal (preferably sodium and potassium) and alkaline earth metal (preferably magnesium and calcium) hydroxides and carbonates. The base is in general employed in an amount of 1 to 20 moles, preferably 1.05 to 10 moles, per mole of indolecarboxylic acid.

The process according to the invention can, for example, be carried out as follows: The reactants are reacted in the chosen reaction medium at the temperature according to the invention. After completion of the reaction, the mixture is worked up in a manner known per se.

Working up is in general effected by separating off the water-soluble constituents by washing with water, filtering and drying the organic phase and, where appropriate, chromatographing over silicon dioxide.

The acemetacin allyl esters according to the invention may be used for the preparation of acemetacin. Acemetacin is a known active substance possessing antiinflammatory properties (Arzneimittelforschung 30, 1314 (1980)).

The preparation of acemetacin from the acemetacin allyl esters is characterized in that the acemetacin allyl esters are reacted in the presence of a phosphine-palladium O-complex and a nucleophilic substance in the temperature range from 10° to 150° C.

Phosphine-palladium O-complex for the process according to the invention are, for example, tetrakis-(triarylphosphine)-palladium O-complexes, for instance the compound

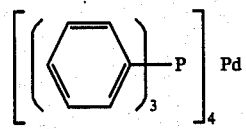 (VII)

in which the phenyl radical can be substituted by other radicals, for example one or two methyl or ethyl groups.

Nucleophilic substances for the process according to the invention are, for example, primary amines, secondary amines or anionic C-H-acidic compounds. Examples of primary and secondary amines are compounds of the formula

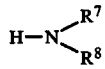 (VIII)

in which
$R^7$ and $R^8$ are identical or different lower alkyl, aryl, cycloalkyl and lower alkenyl, it being possible for $R^7$ and $R^8$ to be linked by an alkylene bridge, which can optionally contain nitrogen, oxygen or sulphur hetero-atoms, and it also being possible for $R^7$ or $R^8$ to denote hydrogen.

The lower alkyl, aryl, cycloalkyl and lower alkenyl radicals conform to the range of meanings given above.

If $R^7$ and $R^8$ are linked by a bridge, 5-membered or 6-membered rings result. In addition to the alkylene members, they can contain one or two identical or different hetero-atoms.

C-H-acidic compounds are, for example, compounds of the formula

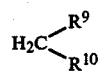 (IX)

in which
$R^9$ and $R^{10}$ are identical or different and denote nitrile, acetyl, benzoyl or alkoxy-($C_1$ to $C_6$)carbonyl, and can optionally be linked by the groups

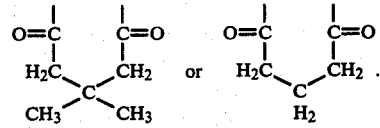

The palladium complex for the process according to the invention is employed in catalytic amount. In general, the palladium complex is employed in an amount of 0.1 to 10 mole %, based on the acemetacin allyl ester.

If tetrakis-triphenylphosphine-palladium is used, the reaction is carried out in a homogeneous phase, using, as the solvent, inert organic solvents, with tetrahydrofuran, 1,4-dioxane, diethyl ether, toluene, chloroform and methylene chloride being preferred. The use of phosphine-palladium (O)-complexes, produced in situ, for this cleavage of the allyl protective groups is also a subject of the invention. For this purpose, a customary hydrogenation catalyst of palladium on charcoal (0.5 to 5% strength) is used and to the palladium (O)-complex is produced in situ by adding a 4 to 5-molar amount (based on palladium) of a triarylphosphine, for example triphenylphosphine. The advantage of this proces is the simplicity of recovery of the noble metal by simple filtration.

The preparation of the acemetacin from the acemetacin allyl ester can, for example, be carried out as follows: the allyl ester, palladium/charcoal and triphenylphosphine are initially introduced into an inert solvent, such as, for example, toluene, and piperidine is added dropwise. The mixture is stirred for several hours at an elevated temperature until the cleavage is completed. The catalyst is then filtered off and the acemetacin is isolated from the filtrate in the usual manner.

It is particularly surprising that acemetacin can, according to the invention, be prepared in high yields and high purities via the acemetacin allyl esters, because neither acidic nor alkaline hydrolysis is carried out, such as is usually employed in the cleavage of protective groups (compare, for example, T. W. Green, Protective Groups in Organic Synthesis, Wiley, N.Y. 1981). Only the allyl ester is cleaved under these conditions, while the activated methyl ester structure remains unaffected.

The acemetacin allyl esters according to the invention possess an outstanding pharmacological action. The use of the acemetacin allyl esters according to the invention in combating inflammation-conditioned disorders and in combating disorders of the rheumatic type, and the use as antiphlogistics, are preferred.

Thus, using the known pharmacological inflammation model, namely the rat paw kaolin oedema (Z. ges. exp. Med. 131, 407 (1959)), results are obtained which correspond to and in part even surpass those with inflammation inhibitors used in pharmacy. Again, in increasing the sulphhydryl group activity of serum proteins, which constitute a measure of the activity of antiphlogistics (Biochem. Pharmacol. 16, 115 (1967)), the majority of the compounds according to the invention were markedly superior to the flufenamic acid used as comparative substance.

The present invention also includes pharmaceutical formulations which, in addition to non-toxic, inert, pharmaceutically suitable excipients, contain one or more active compounds according to the invention, or which consist of one or more active compounds according to the invention, as well as processes for the preparation of these formulations.

By non-toxic, inert, pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary cotaings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fats, and higher esters (for example $C_{14}$-alcohol with $C_{16}$-fatty acid) and waxes, or mixtures of these substances.

Solutions and emulsions can contain, in addition to the active compound or compounds, the customary excipients, such as solvents, solubilizing agents and emulsifiers, for example water, ethylene alcohol, isopropyl alcohol, ethylene carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters or sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethylene alcohol or propylene glycol, suspending agents, for example ethoxylated isostearyl alcohols, polyoxyethylene sorbitol esters and sorbitan esters, micro-crystalline cellulose, aluminum metahydroxide, bentonite, agar-agar and tragacanth, or mixtures of these substances.

The formulation forms mentioned can also contain colorants, preservatives and additives which improve the odor and flavor, for example, peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in human and veterinary medicine, for the prevention, alleviation and/or cure of the abovementioned disorders.

The active compounds or the pharmaceutical formulations can be administered locally, orally, parenterally, intraperitoneally and/or rectally, preferably orally.

In general, it has proved advantageous, both in human medicine and in veterinary medicine, to administer the active compound or compounds according to the invention in total amounts of about 0.1 to 200, preferably 0.5 to 10, mg/kg of body weight every 24 hours, optionally in the form of several individual administrations, in order to achieve the desired results. An individual dose preferably contains the active compound or compounds in amounts of 0.1 to 2.0 mg/kg of body weight. However, it can be necessary to deviate from the dosages mentioned, and in particular to do so as a function of the species and the body weight of the subject to be treated and the nature and severity of the disorder.

EXAMPLE 1

Allyl 1-(4-chlorobenzoyl)-5-methoxy-2-methyl-3-indoleacetoxyacetate (acemetacin allyl ester)

25 g of indometacin, 10 g of potassium carbonate and 1.0 g of benzyltriethylammonium chloride in 140 ml of acetone are stirred for 30 minutes at 50° to 60° C. 10.1 g of allyl chloroacetate are then added dropwise over 5 minutes. The mixture is stirred at 40° C. until the reaction has ended (as checked by thin layer chromatography; about 3 hours). The mixture is filtered while warm, the filtrate is evaporated in vacuo and the residue is taken up in ether (about 90 ml) and mixed with petroleum ether (40 to 60) (about 30 ml). This mixture is left to stand over night at −10° C. and the product is then filtered off and dried in vacuo.

Yield: 28.0 g=87.7% of theory; melting point 59°–61° C.

| $C_{24}H_{22}ClNO_6$ (455.5) | | | | |
|---|---|---|---|---|
| calculated: | C: 63.2 | H: 4.8 | N: 3.1 | Cl: 7.8 |
| found: | 63.1 | 4.9 | 3.1 | 7.6 |

EXAMPLE 2

Cinnamyl 1-(4-chlorobenzoyl)-5-methoxy-2-methyl-3-indoleacetoxyacetate (acemetacin cinnamyl ester)

10 g of indometacin, 4 g of potassium carbonate, 0.3 g of benzyltriethylammonium chloride and 50 ml of acetone are stirred for 30 minutes at 50°–60° C. After addition of 6.32 g of cinnamyl chloroacetate stirring is continued for 3 to 4 hours at 40° C. (check by thin layer chromatography). After filtration, and distilling off the solvent, the residue is recrystallized first from ether/petroleum ether and then from acetone/water.

Yield: 8.6 g=58% of theory; melting point 89°–91° C.

| $C_{30}H_{27}ClNO_6$ (532.0): | | | | |
|---|---|---|---|---|
| calculated: | C 67.7 | H 4.9 | N 2.6 | Cl 6.6 |
| found: | 67.8 | 4.9 | 2.6 | 6.7 |

EXAMPLE 3

Methallyl 1-(4-chlorobenzoyl)-5-methoxy-2-methyl-3-indoleacetoxyacetate (acemetacin methallyl ester)

10 g of indometacin, 4.0 g of potassium carbonate, 0.4 g of benzyltriethylammonium chloride and 60 ml of acetone are stirred for 30 minutes at 56° C. After addition of methallyl chloroacetate, stirring is continued for 3 hours at 40° C. (check by thin layer chromatography). The mixture is filtered and the filtrate is evaporated in vacuo. The residue is dissolved in warm toluene and the insoluble part is filtered off. When the filtrate has cooled, the ester is precipitated with petroleum ether (40–60).

Yield: 11 g=84% of theory; melting point: 74°–76° C.

| $C_{25}H_{24}ClNO_6$ (469.5): | | | | |
|---|---|---|---|---|
| calculated: | C 63.9 | H 5.1 | N 3.0 | Cl 7.5 |
| found: | 64.0 | 5.2 | 3.0 | 7.5 |

EXAMPLE 4

Acemetacin 0.003 mole of tetrakis-triphenylphosphine-palladium-(O) is added to 0.03 mole of acemetacin allyl ester in 50 ml of tetrahydrofuran, under nitrogen. 0.3 mole of piperidine is added dropwise at 20°–25° C., with stirring, and stirring is then continued for 2 hours at room temperature (check by thin layer chromatography). 200 ml of half-concentrated hydrochloric acid are added dropwise with cooling, the phases are separated off, the aqueous phase is extracted twice with methylene chloride and the combined organic phases are evaporated in vacuo. The residue is recrystallised from toluene.

Yield: 86–91% of theory; melting point: 150° C.

EXAMPLES 5 AND 6

On following a procedure analogous to Example 4, acemetacin cinnamyl ester gives 81% of theory, and acemetacin methallyl ester gives 86% of theory, of acemetacin.

EXAMPLE 7

Acemetacin 31.9 g of acemetacin allyl ester, 100 ml of toluene, 2.3 g of triphenylphosphine and 0.75 g of palladium on charcoal (5% strength) are taken as an initial charge, under nitrogen. 11.9 g of piperidine are added dropwise, with stirring, and the mixture is then stirred for a further 3 hours at 90° C. It is filtered hot and the catalyst is rinsed with hot toluene. The filtrate is evaporated, the residue is taken up in methylene chloride (about 300 ml) and this solution is washed with half-concentrated hydrochloric acid (100 ml) and then with water. After removal of the solvent in vacuo, the residue is recrystallized from toluene.

Yield: 27.3 g=94% of theory; melting point: 150°

EXAMPLES 8 AND 9

On following a procedure analogous to Example 7, acemetacin cinnamyl ester gives 89% of theory, and acemetacin methallyl ester gives 84% of theory, of acemetacin.

It will be understood that the specification and examples are illustrative but not limitative of the present invention and that other embodiments within the spirit and scope of the invention will suggest themselves to those skilled in the art.

What is claimed is:

1. An indole derivative of the formula

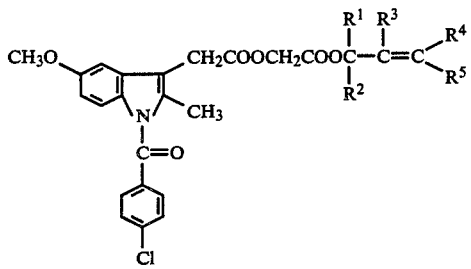

in which
- $R^1$ and $R^2$ each independently is hydrogen or lower alkyl,
- $R^3$ is hydrogen, lower alkyl or halogen, and
- $R^4$ and $R^5$ each independently is hydrogen, lower alkyl, lower alkenyl or aryl of 6 to 12 carbon atoms optionally substituted by halogen or lower alkyl, or $R^2$ and $R^5$ can be linked by an alkylene bridge of the formula $$-CH_2-CH_2-CH_2)_n$$

in which
n is 0 or 1.

2. An indole derivative according to claim 1, wherein such compound is acemetacin allyl ester of the formula

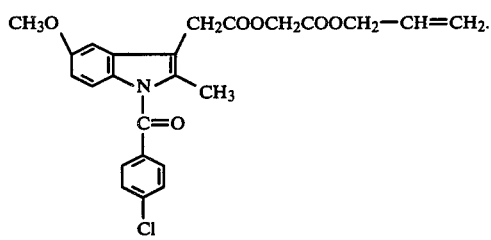

* * * * *